United States Patent
Masue

(10) Patent No.: US 9,040,686 B2
(45) Date of Patent: May 26, 2015

(54) COATING AGENT COMPRISING HYDROXYALKYL CELLULOSE

(75) Inventor: Yusuke Masue, Joetsu (JP)

(73) Assignee: NIPPON SODA CO., LTD., Tokyo (JP)

( * ) Notice: Subject to any disclaimer, the term of this patent is extended or adjusted under 35 U.S.C. 154(b) by 0 days.

(21) Appl. No.: 13/392,298

(22) PCT Filed: Aug. 30, 2010

(86) PCT No.: PCT/JP2010/064686
§ 371 (c)(1),
(2), (4) Date: Feb. 24, 2012

(87) PCT Pub. No.: WO2011/027728
PCT Pub. Date: Mar. 10, 2011

(65) Prior Publication Data
US 2012/0157674 A1      Jun. 21, 2012

(30) Foreign Application Priority Data
Sep. 2, 2009   (JP) ................. 2009-202247

(51) Int. Cl.
*A61K 47/38*  (2006.01)
*A61K 9/28*   (2006.01)
*C09D 101/28* (2006.01)
*C08B 11/08*  (2006.01)

(52) U.S. Cl.
CPC .............. *A61K 47/38* (2013.01); *A61K 9/2866* (2013.01); *C08B 11/08* (2013.01); *C09D 101/284* (2013.01)

(58) Field of Classification Search
CPC ............................ A61K 47/38; A61K 9/2866
See application file for complete search history.

(56) References Cited

U.S. PATENT DOCUMENTS

| 3,131,176 A | * | 4/1964 | Klug ................. 536/85 |
| 3,899,439 A | * | 8/1975 | Mahlman ............ 516/77 |
| 4,154,636 A | * | 5/1979 | Motoyama et al. ........ 156/243 |
| 4,917,885 A | * | 4/1990 | Chiba et al. ........... 206/530 |
| 2006/0182703 A1 | | 8/2006 | Arisz et al. |
| 2009/0030064 A1 | * | 1/2009 | Uchiyama et al. ......... 514/416 |

FOREIGN PATENT DOCUMENTS

| JP | A-9-202801 | 8/1997 |
| JP | A-2001-31701 | 2/2001 |
| JP | A-2002-207030 | 7/2002 |
| JP | A-2007-1873 | 1/2007 |
| JP | A-2007-77242 | 3/2007 |
| JP | A-2008-201713 | 9/2008 |
| JP | A-2008-535937 | 9/2008 |
| WO | WO 2006132360 A1 * | 12/2006 ............... A61K 9/36 |

OTHER PUBLICATIONS

Definition of tablet, Free Merriam-Webster Dictionary, http://www.merriam-webster.com/dictionary/tablet, accessed online on Apr. 30, 2013.*
Guo et al., Pharmaceutical Science & Technology Today, 1998, 1(6), p. 254-261.*
Klucel hydroxypropylcellulose: Physical and Chemical Properties, 2001, Hercules Inc., p. 1-24.*
Alvarez-Lorenzo, et al., Eur. J. Pharm. Biopharm., 2000, 50, p. 307-318.*
Yakuji Nippo Ltd., *Revised Edition Jyakuhin Tenkazai Handbook*, Feb. 28, 2007, pp. 690, 691, 700 and 701.
International Search Report issued in International Application No. PCT/JP2010/064686 on Dec. 7, 2010 (with translation).
Dec. 7, 2010 Written Opinion of the International Searching Authority issued in PCT Application No. PCT/JP2010/064686 (with translation).

* cited by examiner

*Primary Examiner* — Jonathan S Lau
(74) *Attorney, Agent, or Firm* — Oliff PLC

(57) ABSTRACT

A coating agent containing a hydroxyalkyl cellulose in which a content of hydroxyalkoxy groups within the hydroxyalkyl cellulose is within a range of 40 to 50% by mass, preferably a coating agent containing a hydroxyalkyl cellulose in which the content of hydroxyalkoxy groups is within a range of 40 to 50% by mass and also a viscosity of 2% aqueous solution at 20° C. is within a range of 3.0 to 5.9 mPa·s; and a solid preparation coated with the coating agent.

5 Claims, 1 Drawing Sheet

COATING AGENT COMPRISING HYDROXYALKYL CELLULOSE

TECHNICAL FIELD

The present invention relates to a coating agent containing a hydroxyalkyl cellulose. More specifically, the present invention relates to a coating agent suitable for obtaining a coating film of solid preparations for medicine, agricultural chemicals or food.

Priority is claimed on Japanese Patent Application No. 2009-202247, filed Sep. 2, 2009, the content of which is incorporated herein by reference.

BACKGROUND ART

Hydroxypropyl celluloses are non-ionic polymers in which a hydroxyl group in the glucose ($C_6H_{10}O_5$) unit serving as a structural unit of cellulose is etherified with a hydroxypropyl group. With respect to the hydroxypropyl celluloses, those in which the content of hydroxypropoxyl groups is from 53.4 to 77.5% by mass and those in which the content of hydroxypropoxyl groups is from 5 to 16% by mass are known. In general, the latter is called low-substituted hydroxypropyl celluloses (refer to Patent Document 1 or the like).

It has been known to dissolve a hydroxyalkyl cellulose in water to be used as a coating film of solid preparations. However, this coating film of hydroxyalkyl cellulose may cause aggregation called blocking.

Thus, Patent Document 2 has proposed a hydroxypropyl cellulose having an average substitution mole number of 2 to 3, in which the ratio of unsubstituted products and highly substituted products with a substitution mole number of hydroxypropyl groups of 4 or more is low, whereby anti-blocking can be achieved under the environment of 25° C. and 75% RH.

In addition, in Patent Document 3, a coating composition containing a low-substituted hydroxypropyl cellulose, talc, propylene glycol and polyethylene glycol has been proposed, whereby it has been shown that a tablet with no adhesion property can be provided.

CITATION LIST

Patent Documents

[Patent Document 1] Japanese Unexamined Patent Application, First Publication No. 2001-31701
[Patent Document 2] Japanese Unexamined Patent Application, First Publication No. Hei 9-202801
[Patent Document 3] Japanese Unexamined Patent Application, First Publication No. 2007-1873
[Patent Document 4] Japanese Unexamined Patent Application, First Publication No. 2002-207030

SUMMARY OF INVENTION

Technical Problem

However, the conventional coating agents had problems in that the coating film becomes sticky due to moisture absorption which causes blocking under a high temperature and high humidity environment of around 50° C. and 90% RH.

The present invention has an object of providing a coating agent suitable for obtaining a coating film which is less likely to cause blocking even under high temperature and high humidity environments.

Solution to Problem

The inventors of the present invention have conducted intensive and extensive studies in order to achieve the above object. As a result, they discovered that blocking can be prevented even under high temperature and high humidity environments by using a coating agent containing a hydroxyalkyl cellulose in which the content of hydroxyalkoxy groups is within a range of 40 to 50% by mass. The present invention has been accomplished by further studies based on these findings.

That is, the present invention includes the following aspects.
<1> A coating agent containing a hydroxyalkyl cellulose in which the content of hydroxyalkoxy groups within the hydroxyalkyl cellulose is within a range of 40 to 50% by mass.
<2> The coating agent according to the above aspect <1> which is used to coat a tablet.
<3> The coating agent according to the above aspect <1> or <2>, wherein a viscosity of 2% aqueous solution of hydroxyalkyl cellulose at 20° C. is within a range of 3.0 to 5.9 mPa·s,
<4> The coating agent according to any one of the above aspects <1> to <3>, wherein an alkyl group in the hydroxyalkyl cellulose is a propyl group.
<5> A solid preparation coated with the coating agent described in any one of the above aspects <1> to <4>.

Advantageous Effects of Invention

A coating film obtained by using a coating agent according to the present invention hardly causes stickiness and is less likely to cause blocking even when being left to stand under the high temperature and high humidity environment of 50° C. and 90% RH.

Solid preparations coated with a coating agent according to the present invention exhibit almost no adhesion between the preparations even when being left to stand under the high temperature and high humidity environment of 50° C. and 90% RH. In addition, the level of adhesion between the preparation and the vessel is lowered so that the rupture of the coating film when peeling off the preparation from the vessel can be suppressed.

DESCRIPTION OF EMBODIMENTS

Figure 1:
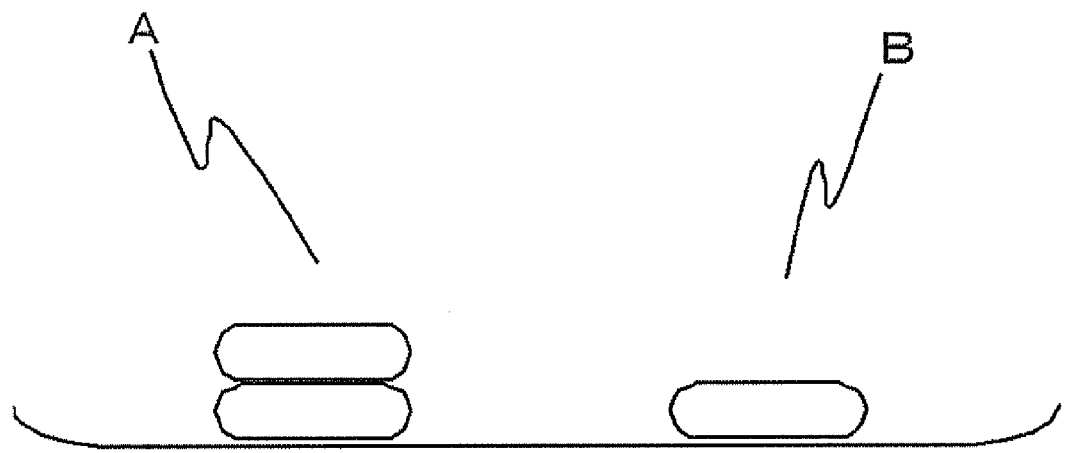
FIG. 1 is a diagram illustrating a method for evaluating the stickiness of coated tablets.

A coating agent of the present invention contains a hydroxyalkyl cellulose.

The hydroxyalkyl cellulose can be obtained, for example, by reacting sodium hydroxide with cellulose serving as a raw material to produce an alkali cellulose, and then allowing a substitution reaction between the alkali cellulose and an alkylene oxide to proceed.

Although examples of the alkylene oxide to be used in the substitution reaction include ethylene oxide, propylene oxide, and the like, propylene oxide is preferable in the present invention. Hydroxypropyl cellulose can be obtained through the substitution reaction by using propylene oxide.

Some or all of the —OH groups in the glucose ring unit of cellulose are substituted with —O—(RO)$_m$—H groups by the substitution reaction. In the formula, R represents a divalent alkyl group. R is preferably CH$_2$—CH(CH$_3$) or CH$_2$—CH$_2$, and more preferably CH$_2$—CH(CH$_3$). m is a natural number of 1 or more. After the substitution reaction, sodium hydroxide can be neutralized by adding acid such as acetic acid or hydrochloric acid to the reaction solution, followed by purification.

The hydroxyalkyl cellulose included in the coating agent of the present invention is in such a manner that the content of hydroxyalkoxy group therein is within a range of 40 to 50% by mass, and preferably within a range of 42 to 48% by mass. When the content of hydroxyalkoxy group is within the range, stickiness of the coating film is reduced, which makes the blocking less likely. It should be noted that the content of hydroxyalkoxy group can be determined in accordance with the method based on USP24 (US Pharmacopeia) or the method described in Patent Document 4.

The hydroxyalkyl cellulose used in the present invention has a viscosity at 20° C. in a 2% aqueous solution, which is preferably within a range of 2.0 to 10.0 mPa·s, and more preferably within a range of 3.0 to 5.9 mPa·s. Viscosity is an index indicating the degree of polymerization of hydroxyalkyl cellulose. If the viscosity is within the above range, the workability when obtaining granular agents or tablets is improved.

The coating agent of the present invention is obtainable by dissolving or dispersing the aforementioned hydroxyalkyl cellulose in a solvent.

Water is usually used as the solvent. An organic solvent, such as acetone, ethanol or isopropyl alcohol, may also be used.

Although the content of the aforementioned hydroxyalkyl cellulose in the coating agent of the present invention is not particularly limited, it is usually at least 0.5% by mass, and preferably at least 1.0% by mass, relative to the dry mass of the coating agent.

In the coating agent of the present invention, a known compounding agent that can be blended into coating agents for tablets may be incorporated, in addition to the aforementioned hydroxyalkyl cellulose. Examples thereof include powders such as talc, titanium oxide, ferric oxide yellow, iron sesquioxide, legal pigments, light anhydrous silicic acid and hydrous silicon dioxide; lubricants such as polyethylene glycol, polypropylene glycol, triethyl citrate, glycerol mono-, di- or tri-acetate and 1,2-propylene glycol; adhesion promoters such as sucrose, polyvinylpyrrolidone, dextrose, sorbitol, mannitol, sucrose, polyvinylpyrrolidone, lactose, starch, sodium starch glycolate, ethyl cellulose and maltodextrins; and film forming agents such as cellulose acetate phthalate, microcrystalline cellulose, methyl cellulose, hydroxypropyl methylcellulose, alginates, gum arabic, carboxymethyl cellulose, hydroxyethyl cellulose and methyl cellulose.

Plain tablets or granulated materials that are coated with the coating agent of the present invention are prepared by the usual production method. For example, a plain tablet of suitable size can be obtained by mixing and kneading drugs and excipients, binders, disintegrants, lubricants or the like with a small amount of water, organic solvents or the like, followed by the steps of granulation, drying, particle size control and, if necessary, tableting.

It should be noted that the coating can usually be carried out using a sugar coating pan or a porous coating machine, usually at room temperature, or while heating to 20 to 200° C. in some cases.

Examples of the form of the solid preparation to be obtained include coated tablets, coated granules and coated grains.

Moreover, the solid preparation obtained in the present invention can be prepared as a sugar-coated tablet or the like. Furthermore, if the gloss is required, wax coating can be conducted with carnauba wax or the like in accordance with the conventional methods.

EXAMPLES

Next, the present invention is described in more detail, based on a series of examples. However, the present invention is in no way limited by these examples.

[Production of Hydroxypropyl Cellulose]

176 g of ground pulp was placed into a reactor equipped with a stirrer, and then 68.2 g of a 20% aqueous NaOH solution was added thereto, followed by the addition of 602 g of toluene. The resulting mixture was stirred for 30 minutes and the temperature inside the reactor was adjusted to 30° C. A mercerization reaction was conducted for 1 hour by applying pressure with nitrogen while stirring inside the reactor.

After releasing the pressure, propylene oxide was added thereto, and the temperature inside the reactor was increased to about 80° C. An etherification reaction was carried out by maintaining the temperature at 80° C. for about 1 hour with stirring. Then, the temperature inside the reactor was lowered to 45° C. or less. After 1 hour from the start of the cooling, the temperature was raised to 85° C. and was maintained at 85° C. for 1.5 hours. Then, the temperature inside the reactor was lowered to 40° C. or less.

The product was washed out from the reactor with boiling water. The product obtained by washing was placed in a flask, and toluene was removed by distillation. After distillation, the resulting solution was allowed to stand. A gel was precipitated. The supernatant was decanted.

Boiling water was poured onto the gel, and the resultant was stirred for 10 minutes and was then allowed to stand again. A gel was precipitated. The supernatant was decanted. Boiling water was poured onto the gel. 60% acetic acid was then added thereto every few tens of minutes with stirring at about 85° C. until the pH of 4.9 or less was achieved. The temperature of the resultant was then adjusted to 90° C., and a predetermined amount of viscosity modifier was added thereto with stirring. The resulting mixture was stirred for 14 hours at 90° C.

A 20% aqueous NaOH solution was then added thereto every few tens of minutes with stirring at about 85° C. until the pH of 7.5 was achieved. The resulting solution was then allowed to stand. A gel was precipitated. The supernatant was decanted. Boiling water was poured onto the gel. The resultant was stirred for 10 minutes and was then allowed to stand again. A gel was precipitated. The supernatant was decanted.

The gel was collected from the flask and cast on a flat plate made of fluorine resin. The resultant was vacuum dried at 70° C.

In this manner, hydroxypropyl cellulose was obtained.

It should be noted that the added amount of propylene oxide in the above etherification reaction was set to 5.99 and 4.28 in terms of the molar ratio relative to the pulp. The content of hydroxypropoxy groups within the obtained hydroxypropyl cellulose was 56.6% by mass and 45.7% by mass, respectively. The viscosity in the 2% aqueous solution at 20° C. was 5.8 mPa·s and 4.8 mPa·s, respectively. Note that the viscosity of 2% aqueous solution was measured at 20° C. and 60 rpm using a digital viscometer/B-type viscometer (DV-II+Pro, manufactured by Brookfield Engineering Laboratories).

[Coating Evaluation]

70 parts by weight of lactose, 30 parts by weight of cornstarch, 3 parts by weight of hydroxypropyl cellulose (HPC-L product, manufactured by Nippon Soda Co., Ltd.) and 2 parts by weight of sugar esters were mixed, and then subjected to tableting and molding to obtain plain tablets, with each tablet weighing about 180 mg. The plain tablets exhibited a tablet hardness of 6.8 Kg and a disintegration time of 10.3 minutes.

150 g of the plain tablets were coated with the 8% aqueous solution of hydroxypropyl cellulose (HPC having a solid content of 3%) obtained as described above, using the fully automated sugar coating/film coating machine (New Hi-Coater HCT-MINI; manufactured by Freund Corporation).

The above hardness was obtained as an average value of 20 tablets using the ERWEKA Hardness Tester (TBH28 model, manufactured by ERWEKA GmbH), and the above disintegration time was obtained by measuring an average disintegration time of 6 tablets under the conditions of distilled water and 37° C. using a disintegration tester (NT-2 type, manufactured by Toyama Sangyo Co., Ltd.).

[Stickiness Evaluation of Coated Tablet]

The obtained coated tablets were placed in a Petri dish either in a stacked arrangement of two tablets (A) or in an arrangement of single tablet (B), as shown in FIG. 1, and each of the 5 sets was left to stand in an environment of 50° C. and 90% RH.

The adhesion status of the coated tablets was observed and the moisture absorption rate of the coated tablets was also measured after the coated tablets were left to stand for 1 hour, 2.5 hours, 4.5 hours and 24 hours. With respect to the moisture absorption rate, the tablets that were left to stand in an environment of 50° C. and 90% RH were taken out at each time point, and the weight increase was measured to calculate the weight percentage of the increase as the moisture absorption rate.

The results are shown in Table 1.

TABLE 1

| Coating agent | | Comparative Example | Example according to the present invention |
|---|---|---|---|
| Content of hydroxypropoxy group [% by mass] | | 56.6 | 45.7 |
| Viscosity [mPa · s] | | 5.8 | 4.8 |
| Coated tablet | | | |
| Tablet hardness [Kg] | | 7.8 | 8.2 |
| Disintegration time [min] | | 10.1 | 10.6 |
| Stickiness evaluation | | | |
| Stacked arrangement of two tablets | 1 hour | No adhesion | No adhesion |
| | 2.5 hours | Slight adhesion Adhesion in 2 sets out of 5 sets | Slight adhesion Adhesion in 1 set out of 5 sets |
| | 4.5 hours | Adhesion Adhesion in all 5 sets | Slight adhesion Adhesion in 3 sets out of 5 sets |
| | 24 hours | Adhesion Adhesion in all 5 sets | Slight adhesion No adhesion in some cases |
| Arrangement of single tablet | 1 hour | No adhesion | No adhesion |
| | 2.5 hours | Slight adhesion Adhesion mark at the center | Little adhesion No adhesion mark |

TABLE 1-continued

| Coating agent | | Comparative Example | Example according to the present invention |
|---|---|---|---|
| | 4.5 hours | Adhesion Surface rupture | Slight adhesion Adhesion mark at the center |
| | 24 hours | Adhesion Surface rupture | Adhesion Partial rupture |
| Moisture absorption rate | 1 hour | 3.7% | 3.5% |
| | 2.5 hours | 4.4% | 4.4% |
| | 4.5 hours | 4.5% | 4.6% |
| | 24 hours | 4.6% | 4.8% |

There was no difference between the Example according to the present invention and Comparative Example in terms of tablet hardness, disintegration time and moisture absorption rate.

5 sets of coated tablets of Comparative Example that were arranged in a stack of two tablets were all adhered to each other after 4.5 hours had elapsed. On the other hand, the coating agent in the Example according to the present invention which was arranged in a stack of two tablets was only slightly adherent even when 24 hours had elapsed.

Figure 2A:
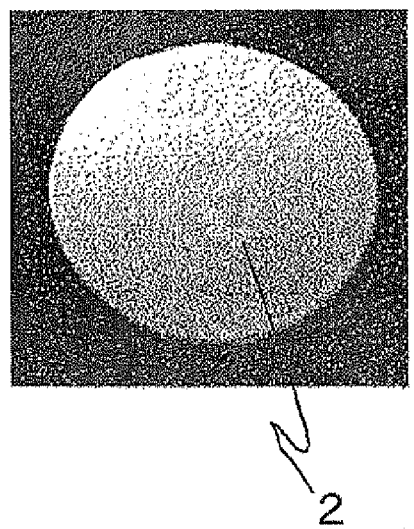
FIG. 2A is a diagram showing the surface of a coated tablet of Comparative Example after a single tablet was being arranged in a Petri dish and left to stand for 24 hours under an environment of 50° C. and 90% RH.
Figure 2B:
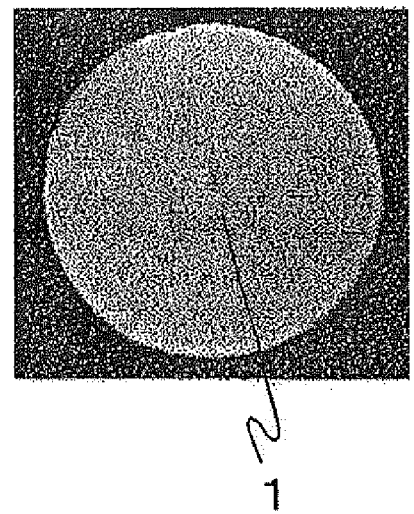
FIG. 2B is a diagram showing the surface of a coated tablet according to the present invention after a single tablet was being arranged in a Petri dish and left to stand for 24 hours under an environment of 50° C. and 90% RH.

The coated tablet of Comparative Example in a single tablet arrangement was adhered to the Petri dish enough to leave an adhesion mark when 2.5 hours had elapsed, and was adhered so that the surface thereof was ruptured considerably in a crater-like manner when 4.5 hours had elapsed (FIG. 2A). On the other hand, the coating agent in the Example according to the present invention in a single tablet arrangement was adherent to leave an adhesion mark only when 4.5 hours had elapsed, and was adherent so that only a portion of the surface thereof was ruptured even when 24 hours had elapsed (FIG. 2B).

INDUSTRIAL APPLICABILITY

A coating film obtained by using a coating agent of the present invention hardly causes stickiness and is less likely to cause blocking even when left to stand under the high temperature and high humidity environment of 50° C. and 90% RH. Further, solid preparations coated with a coating agent of the present invention exhibit almost no adhesion between the preparations even when being left to stand under the high temperature and high humidity environment of 50° C. and 90% RH. In addition, the level of adhesion between the preparation and the vessel is lowered so that the rupture of the coating film when peeling off the preparation from the vessel can be reduced.

REFERENCE SIGNS LIST

A Stacked arrangement of two tablets
B Arrangement of single tablet
1 Adhesion mark
2 Rupture

The invention claimed is:
1. A coating agent comprising:
    a solvent consisting of water; and
    a hydroxypropyl cellulose in which:
        a content of hydroxypropoxy groups within the hydroxypropyl cellulose is within a range of 42 to 48% by mass; and
        a viscosity of a 2% aqueous solution of the hydroxypropyl cellulose at 20° C. is within a range of 3.0 to 5.9 mPa·s.

2. The coating agent according to claim 1, consisting of:
the solvent;
the hydroxypropyl cellulose; and
at least one selected from the group consisting of talc, titanium oxide, ferric oxide yellow, iron sesquioxide, legal pigments, light anhydrous silicic acid, hydrous silicon dioxide, polyethylene glycol, polypropylene glycol, triethyl citrate, glycerol mono-acetate, glycerol di-acetate, glycerol tri-acetate, 1,2-propylene glycol, sucrose, polyvinyl pyrrolidone, dextrose, sorbitol, mannitol, sucrose, polyvinyl pyrrolidone, lactose, starch, sodium starch glycolate, ethyl cellulose, maltodextrins, cellulose acetate phthalate, microcrystalline cellulose, hydroxypropyl methylcellulose, alginates, gum arabic, carboxymethyl cellulose, hydroxyethyl cellulose, and methyl cellulose.

3. A solid preparation comprising a coating film obtained using the coating agent of claim 1.

4. The solid preparation according to claim 3, further comprising a plain tablet comprising a drug.

5. The solid preparation according to claim 3, wherein the solid preparation is a sugar-coated tablet.

* * * * *